(12) United States Patent
Burkhart et al.

(10) Patent No.: US 11,737,744 B2
(45) Date of Patent: Aug. 29, 2023

(54) SLACK REDUCING SUTURE ANCHOR ASSEMBLY AND METHOD OF TISSUE REPAIR

(71) Applicant: Arthrex, Inc., Naples, FL (US)

(72) Inventors: Stephen S. Burkhart, Boerne, TX (US); Derek C. Sullivan, Naples, FL (US); Andrew C. Petry, Naples, FL (US)

(73) Assignee: Arthrex, Inc., Naples, FL (US)

( * ) Notice: Subject to any disclaimer, the term of this patent is extended or adjusted under 35 U.S.C. 154(b) by 851 days.

(21) Appl. No.: 16/521,919

(22) Filed: Jul. 25, 2019

(65) Prior Publication Data

US 2021/0022725 A1    Jan. 28, 2021

(51) Int. Cl.
*A61B 17/04*    (2006.01)

(52) U.S. Cl.
CPC .... *A61B 17/0401* (2013.01); *A61B 2017/044* (2013.01); *A61B 2017/0445* (2013.01); *A61B 2017/0453* (2013.01); *A61B 2017/0496* (2013.01)

(58) Field of Classification Search
CPC ........ A61B 17/0401; A61B 2017/0409; A61B 2017/0414; A61B 2017/044; A61B 2017/0445; A61B 2017/0412; A61B 2017/0458; A61B 2017/0403; A61B 2017/0464; A61B 2017/045; A61B 2017/0453; A61B 2017/0438; A61B 2017/0427; A61B 2017/0456; A61B 2017/0425; A61B 2017/0451; A61B 2017/0424; A61B 2017/0448; A61B 2017/0446; A61B 2017/0441; A61B 2017/0454; A61B 2017/0475; A61B 2017/0408; A61B 2017/042; A61B 2017/0417; A61B 2017/0406

See application file for complete search history.

(56) References Cited

U.S. PATENT DOCUMENTS

| | | | |
|---|---|---|---|
| 4,870,957 A * | 10/1989 | Goble | A61B 17/686 623/13.12 |
| 5,827,285 A * | 10/1998 | Bramlet | A61B 17/80 606/328 |
| 6,267,766 B1 | 7/2001 | Burkhart | |
| 6,517,542 B1 * | 2/2003 | Papay | A61F 2/0811 606/232 |
| 6,540,750 B2 | 4/2003 | Burkhart | |
| 7,955,388 B2 * | 6/2011 | Jensen | A61B 17/8685 623/13.14 |
| 7,959,649 B2 | 6/2011 | Burkhart | |
| 8,545,535 B2 * | 10/2013 | Hiratsuka | A61B 17/0401 606/232 |
| 8,777,990 B2 | 7/2014 | van der Burg et al. | |
| 9,005,246 B2 | 4/2015 | Burkhart et al. | |

(Continued)

*Primary Examiner* — Dianne Dornbusch
(74) *Attorney, Agent, or Firm* — Blank Rome LLP

(57) ABSTRACT

Surgical anchor assemblies and method of tissue repair using the same. The surgical anchor assemblies have a cannulated fixation device, an implant configured to be coupled to the fixation device, and a stop mechanism for preventing relative movement between the fixation device and the implant, such that the fixation device and the implant are configured to rotate together, and a flexible strand winds up to reduce any slack in the flexible strand used for the repair.

21 Claims, 5 Drawing Sheets

(56) References Cited

U.S. PATENT DOCUMENTS

| | | | |
|---|---|---|---|
| 9,277,909 B2 * | 3/2016 | Brunsvold | A61B 17/0401 |
| 9,924,935 B2 | 3/2018 | Housman | |
| 10,045,770 B2 | 8/2018 | Burkhart et al. | |
| 2003/0065390 A1 * | 4/2003 | Justin | A61F 2/0811 |
| | | | 606/65 |
| 2004/0093030 A1 * | 5/2004 | Cox | A61B 17/0401 |
| | | | 606/232 |
| 2006/0276841 A1 * | 12/2006 | Barbieri | A61B 17/0401 |
| | | | 606/232 |
| 2009/0312793 A1 * | 12/2009 | Huxel | A61B 17/0401 |
| | | | 606/232 |
| 2010/0049249 A1 | 2/2010 | Lombardo | |
| 2013/0035721 A1 | 2/2013 | Brunelle | |
| 2014/0277129 A1 | 9/2014 | Arai et al. | |
| 2014/0364905 A1 * | 12/2014 | Lunn | A61B 17/0401 |
| | | | 606/232 |
| 2014/0364906 A1 * | 12/2014 | Palese | A61B 17/0401 |
| | | | 606/232 |

* cited by examiner

SLACK REDUCING SUTURE ANCHOR ASSEMBLY AND METHOD OF TISSUE REPAIR

FIELD OF THE INVENTION

The present invention relates to a suture anchor assembly and method of tissue repair designed to reduce slack in the suture during the repair.

BACKGROUND

When soft tissue, such as tendons and ligaments, is torn away from the bone, surgery, such as arthroscopic surgical techniques, may be required to repair the tear and reattach the tissue to bone. Typically, a suture is threaded through the torn tissue and through a suture anchor in a tunnel or hole drilled into the bone. The suture can be drawn up and tensioned to approximate the torn tissue against the bone in proper position to heal.

Suture anchors are devices that are typically insertable arthroscopically through a cannula to the repair site and then implanted to anchor the repair suture to bone. That is, the repair suture is passed through the soft tissue and through the suture anchor to reattach the tissue to bone. Such a suture anchor assembly is disclosed in commonly owned U.S. Pat. Nos. 9,005,246 and 10,045,770, the subject matter of each of which is incorporated by reference.

One known tendon repair technique using suture anchors, namely Arthrex's SutureBridge®, is disclosed in commonly assigned U.S. Patent Publication No. 2007/0191849, the disclosure of which is herein incorporated by reference, has a tied medial row constructed with two threaded suture anchors, combined with knotless lateral fixation using two anchors, such as two of Arthrex's PushLock® anchors. The technique enhances footprint compression and promotes tendon healing-to-bone with minimal knot tying. Another known tissue repair technique, namely Arthrex's Speed-Bridge®, uses a threaded swivel anchor (such as disclosed in U.S. Patent Publication No. 2008/0004659, the disclosure of which is herein incorporated by reference) combined with FiberTape® (disclosed in U.S. Patent Publication No. 2005/0192631, the disclosure of which is herein incorporated by reference) to create a quick and secure bridge construct, as discussed above, with no knots and minimal suture passing steps.

Securing suture during surgery using known techniques can sometimes be difficult, if the repair suture is loose and slack remains in the suture or repair construct, particularly after installation of the suture anchor in bone. Accordingly, a need exists for a suture anchor assembly and tissue repair technique that effectively reduces any slack in the suture used for tissue repair.

SUMMARY OF THE INVENTION

Accordingly, the present invention may provide a surgical anchor assembly that comprises a fixation device having a proximal end, a distal end, a cannulation extending therethrough, and a first engagement feature at or near the distal end. An implant of the surgical anchor assembly may comprise a first portion connectable to the distal end of the fixation device and a second engagement feature engageable with the first engagement feature, and a second portion configured to capture a flexible strand. A stop mechanism may be configured to prevent rotational movement between the fixation device and the implant in at least one direction when the implant is connected to the fixation device.

In certain embodiments, the first portion of the implant is insertable into the distal end of the fixation device; the first engagement feature is formed in the cannulation of the fixation device, and the second engagement feature is formed on an outer surface of the first portion of the implant; the first and second engagement features facilitate a limited rotational connection between the fixation device and the implant, and the stop mechanism is configured to stop the rotational movement facilitated by the first and second engagement features; the stop mechanism is formed in the cannulation of the fixation device at or near the distal end section; the first and second engagement features each comprises a thread; an end of the thread of the first engagement feature defines the stop mechanism; when the implant and the fixation device are connected with the stop mechanism preventing rotation therebetween, the second portion of the implant remains outside of and extends away from the distal end of the fixation device; the second portion of the implant comprises an eyelet for capturing the flexible strand; an exterior surface of the fixation device comprises an engagement feature for engaging a bone hole; and/or the engagement feature on the exterior surface of the fixation device comprises a thread.

The present invention may also provide a surgical anchor assembly that comprises a fixation device having a proximal end, a distal end, a cannulation extending therethrough, and an exterior surface with a first engagement feature for engaging a bone hole. An implant of the surgical anchor assembly may comprise a first portion connectable to the distal end of the fixation device in a rotationally fixed manner and a second portion configured to capture a flexible strand. A separate piggyback fixation piece may further be connectable to the proximal end of the fixation device to extend a total length of the surgical anchor assembly, where an exterior surface of the piggyback fixation piece comprises a second engagement feature that is complementary to the first engagement feature on the exterior surface of the fixation device for engaging the bone hole.

In certain embodiments, the fixation device and the piggyback fixation piece comprise the same material; the fixation device and the piggyback fixation piece comprise different materials; the piggyback fixation piece has a shorter length than a length of the fixation device; the first and second engagement features each comprises a thread, and the thread of the second engagement feature is alignable with the thread of the first engagement feature; and/or the implant is rotatably connectable to the fixation device in a limited manner, and a stop mechanism is configured to stop the rotational movement in at least one direction resulting in the rotationally fixed connection.

The present invention may also provide a method of tissue repair using a surgical anchor assembly that may comprise a fixation device having a proximal end, a distal end, a cannulation extending therethrough, and a first engagement feature at or near the distal end, an implant comprising a first portion connectable to the distal end of the fixation device and having a second engagement feature engageable with the first engagement feature, and a second portion, and a flexible strand. The method may comprise the steps of advancing the implant in a bone hole when the flexible strand is captured by the second portion of the implant; advancing the fixation device over the implant to connect the implant to the fixation device, where a stop mechanism prevents rotational movement between the fixation device and the implant in at least one direction; and rotating the fixation device and the implant together in the at least one direction to wrap the flexible strand around at least one of the implant or the fixation device for reducing slack in the flexible strand.

In certain embodiments, the first and second engagement features each comprises a thread, and the step of advancing the fixation device over the implant comprises threadably engaging the fixation device with the implant. In certain embodiments, the method further comprises at least one of the following additional steps: using an inserter to advance the implant in the bone hole and to advance the fixation device, where the inserter is configured to extend through the cannulation of the fixation device, and where an end of the inserter is configured to hold the implant; threading the flexible strand through or around tissue prior to rotating the fixation device and the implant together to reduce the slack in the flexible strand; stacking a piggyback fixation piece on the proximal end of the fixation device prior to rotating the fixation device and the implant together to reduce the slack in the flexible strand; removing portions of the piggyback fixation piece that protrude outside of the bone hole after rotating the fixation device and the implant together to reduce the slack in the flexible strand; forming the bone hole prior to advancing the implant, where the bone hole has a cylindrical profile with a length that is at least a combined length of the fixation device and the implant when the implant is connected to the fixation device; and/or forming the bone hole prior to advancing the implant, where the bone hole has a cylindrical profile with a conically shaped distal end, and where the length of the cylindrical portion of the bone hole is at least a combined length of the fixation device and the implant when the implant is connected to the fixation device.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawing figures.

DETAILED DESCRIPTION

Figure 3:
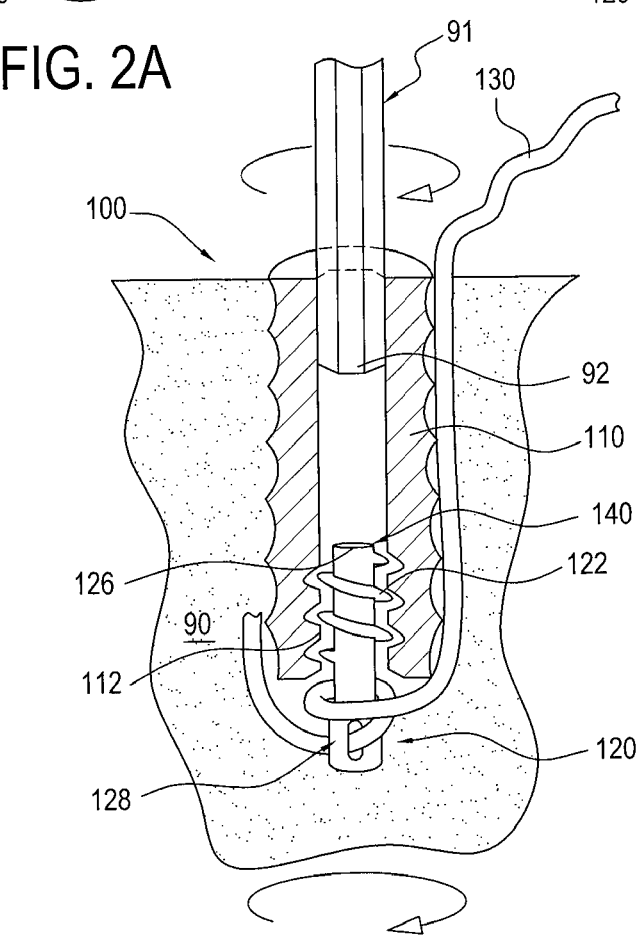
FIG. 3 is a cross-sectional view of the anchor assembly illustrated in FIGS. 1A and 1B, showing the anchor assembly installed in bone with a flexible strand thereof being wound to reduce slack in the flexible strand.

Referring to the figures, the present invention generally relates to a suture anchor assembly 100 and method of tissue repair designed to enable reduction of residual slack in the repair suture, tape, or flexible strand during a tissue repair procedure. Suture anchor assembly 100 may generally include a cannulated fixation device 110 that has an inner engagement feature 112, an implant 120 that captures one or more repair flexible strands 130 and may be rotatably coupled to the fixation device 110, wherein the implant 120 has an outer engagement feature 122 corresponding to the inner engagement feature 112, and a stop mechanism 140 that is associated with the inner and outer engagement features 112 and 122. Stop mechanism 140 stops or prevents further rotation and/or other relative movement between the fixation device 110 and the implant 120 to unify the same such that the unified fixation device 110 and implant 120 can be rotated together to wind up and reduce or take up any slack or redundancy in the repair suture, tape, or flexible strand during a repair of the tissue, as seen in FIG. 3.

Figure 1A:
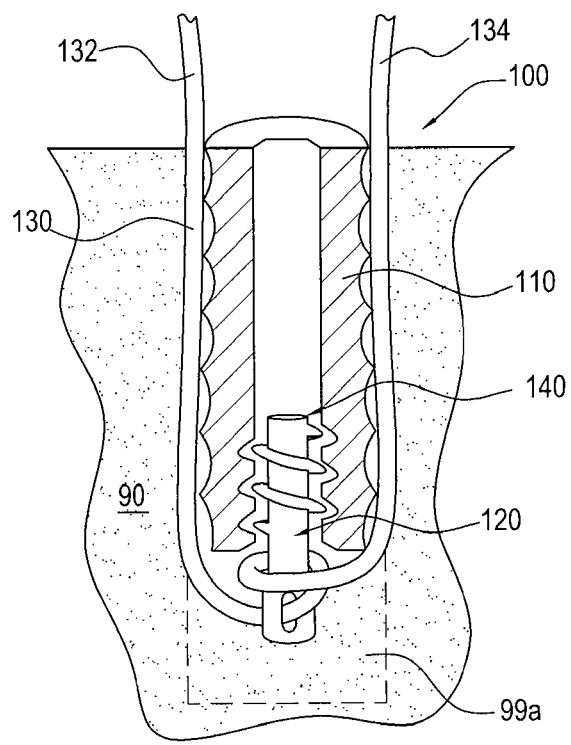
FIGS. 1A and 1B are cross-sectional views of a slack reducing surgical anchor assembly according to an exemplary embodiment of the present invention, showing the anchor assembly installed in a cylindrical bone hole or a conical bone hole, respectively.
Figure 1B:
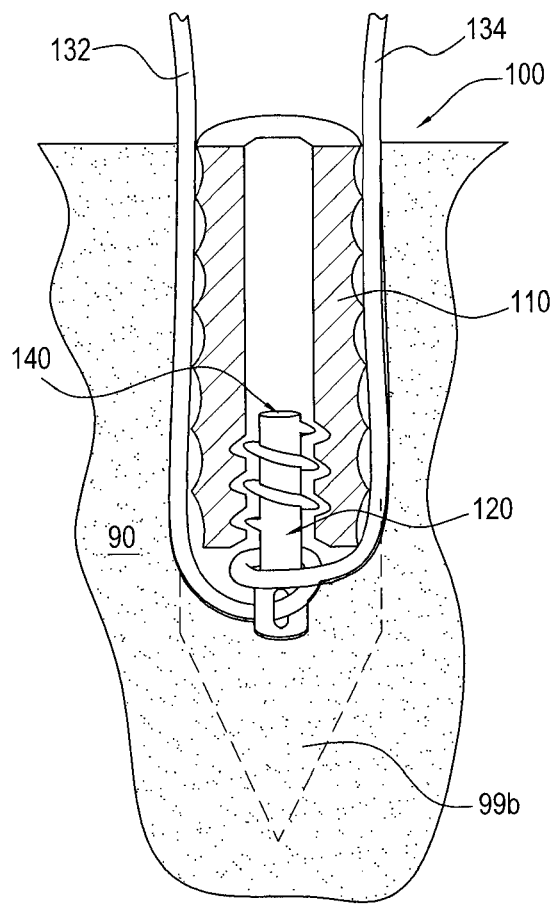

Fixation device 110 may have a proximal end section 114, a distal end section 116, and a cannulation 118 therethrough, with the inner engagement feature 112 being disposed in the cannulation 118 at the distal end section 116. Fixation device 110 has a fixation exterior surface 119 configured to engage bone 90, such as via a bone hole or bone socket 99a, 99b, as seen in FIGS. 1A and 1B, respectively. Bone socket 99a (FIG. 1A) is preferably elongated with, for example, a cylindrical shape or profile. A bone socket with such cylindrical profile that extends all the way to the distal end of the bone socket can be formed, for example, with a headed reamer or a second-stage punch. In some embodiments, a blunt punch or a modified flip-cutter drill can be used to make the distal region of the bone socket more spacious, without compromising the structure of the more proximal regions of the bone socket. A different bone socket 99b (FIG. 1B) is also preferably elongated with, for example, a cylindrical shape or profile, and further having a cone shaped bottom. This type of bone socket can be formed simply with a longer conical punch. The conical bottom of bone socket 99b may also be formed to be more elongate than typical, for example, with a separate conical punch with a more elongate profile. Generally, the length of the cylindrical portions of the bone sockets 99a, 99b are formed to be approximately the same or greater than a combined length of the unified fixation device 110 and implant 120, so that the bone socket remains cylindrical at an axial level of the implant 120, before additional advancement is performed as described in greater detail below. Both bone socket arrangements 99a, 99b may better accommodate suture anchor assemblies according to embodiments of the invention. It is noted, however, that suture anchor assemblies according to embodiments of the invention can also be accommodated in more traditionally shaped bone holes or bone sockets, or more generally, bone holes with profiles that differ from those of bone sockets 99a, 99b. Fixation exterior surface 119 may comprise, for example, exterior threads or ridges, or be any known anchoring surface, for engaging and anchoring into the bone. Implant 120 is preferably rotatably coupled to the distal end section 116 of fixation device 110. Implant 120 may comprise a body 124 that has at least first and second portions 126 and 128, where the first portion 126 may be configured to be receivable in the distal end section 116 of fixation device 110 and the second portion 128 may be configured to capture at least one flexible strand 130. The second portion 128 may include, for example, an eyelet 129 or the like capable of capturing the flexible strand 130.

Figure 2A:
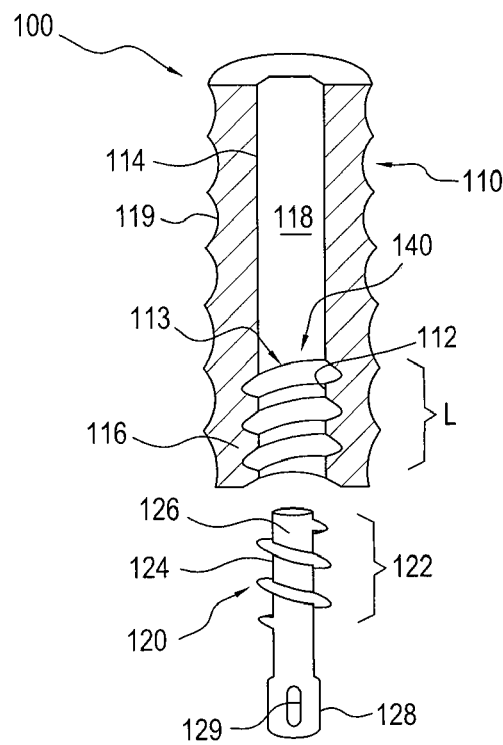
FIGS. 2A and 2B are exploded and assembled cross-sectional views, respectively, of the anchor assembly illustrated in FIGS. 1A and 1B.
Figure 2B:
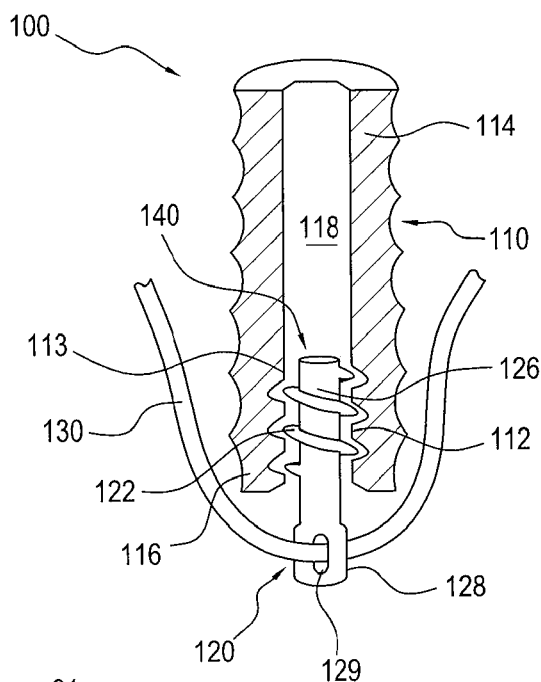

Stop mechanism 140 may be any structure that provides a hard stop and prevents further rotation and/or other relative movement between the fixation device 110 and the implant 120. And the stop mechanism 140 may be incorporated into either the inner engagement member 112 of fixation device 110 or the outer engagement member 122 of the implant 120. In an exemplary embodiment, stop mechanism 140 is disposed in the cannulation 118 of the fixation device, at the distal end section 116. Here, the inner engagement member 112 of the fixation device may be internal threads with a pre-determined limited distance or length L, where the end 113 of that predetermined length L forms the stop mechanism 140, as best seen in FIGS. 2A and 2B. That is, when implant 120 is being coupled to the distal end section 116 of fixation device 110, the outer threads 122 of the implant 120 will engage the inner threads 112 of fixation device 110, thereby threadably coupling the same until the implant's outer threads 122 reach the end 113 of the fixation device's inner threads 112. The end 113 of the inner threads 112 of the fixation device then prevents further relative movement (e.g., rotation or swiveling) between the implant 120 and the fixation device 110, such that the implant 120 and fixation device 110 form a single unit and can be rotated together (i.e., at the same rate as one another) due to the engagement therebetween. As such, after engagement at the stop mechanism 140, additional rotational advancement or driving of fixation device 110, for example, clockwise into the bone hole will also result in rotational advancement of the implant 120 as well, causing the flexible strand 130 that is captured in eyelet 129 to wrap around the assembly and tighten. Other known engagement features may be used instead, such as bayonet or snap engagement, or the like, with the stop mechanism 140 being either incorporated into the engagement between the fixation device 110 and the implant 120 or separate from that engagement.

Figures 4, 5A:
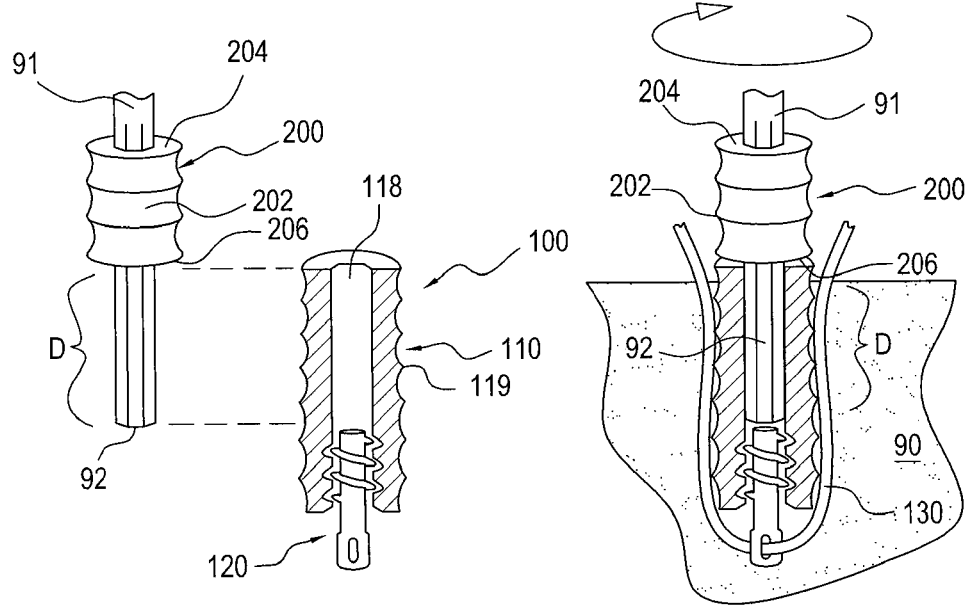
FIG. 4 is an exploded cross-sectional view of a slack reducing surgical anchor assembly according to another exemplary embodiment of the present invention.
FIG. 5A is an assembled cross-sectional view of the anchor assembly illustrated in FIG. 4, showing the anchor assembly being installed into a bone hole.
Figure 5B:
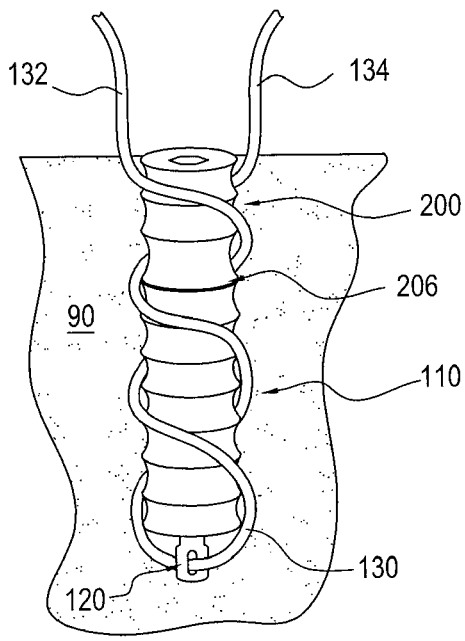
FIG. 5B is a side elevational view of the anchor assembly illustrated in FIG. 5A, showing the anchor assembly fully installed in the bone hole.

FIGS. 4, 5A and 5B illustrate another exemplary embodiment of the present invention. Ideally, in a fully implanted configuration, a proximal end of fixation device 110 is positioned substantially flush with the surface of the bone, to maximize fixation between the suture anchor assembly 100 with the bone, especially cortical bone. In some cases where additional tightening of the flexible strand 130 is desired via additional rotation of fixation device 110, suture anchor assembly 100 will advance further into the bone and engage less solid regions of the bone, while contact between the distal end of fixation device 110 and cortical bone will be reduced. In such situations, a piggyback anchor or fixation piece 200 may serve as an extension of the anchor that is attached to or otherwise added to the proximal end of the fixation device 110 to essentially lengthen the fixation device 110 to ensure that the threads of the suture anchor assembly 100 as a whole engage cortical bone for better anchoring of the combined assembly 100 in the bone socket. Piggyback fixation piece 200 may be similar to the fixation device 110, except with a shorter length. A fixation exterior surface 202 of piggyback fixation piece 200 may be complementary to that of the fixation device 110, such as exterior threads or ridges. Piggyback fixation piece 200 may be cannulated, and either end 204 or 206 of piggyback fixation piece 200 may be stacked on the proximal end section 114 of fixation device 110, as seen in FIG. 5A. In FIG. 4, the piggyback fixation piece 200 has been placed over an inserter 91, which in turn extends entirely through and out of the distal end 206 of the piggyback fixation piece 200. The fixation device 110 and the piggyback fixation piece 200 may be formed of the same or different materials. Exemplary materials may include polyether ether ketone (PEEK), bioabsorbable material, biocomposite material, metal, and the like.

In some embodiments, the distal end 206 of piggyback fixation piece 200 may include an engagement feature to axially and/or rotationally lock with the proximal end of fixation device 110, to provide for a more secure fixation between the respective parts. In yet another alternative embodiment of the piggyback anchor, rather than having a piggyback anchor that is fully cannulated and placed over a separate driver or inserter, where the end of the driver or inserter interacts with the cannulation of the fixation device 110, a distal end of the piggyback anchor itself may include a projection configured to be form-fit into the cannulation of the fixation device, for example, with matching hex profiles. Here, a tool recess may instead be formed at the proximal end of the piggyback anchor, so that a tool can be used to effect rotation of the piggyback anchor, while the piggyback anchor effects rotation of both the fixation device and implant via the form-fit with the fixation device.

A method of tissue repair according to the present invention may comprise the initial steps of installing the implant 120 in the prepared bone hole or socket 99a or 99b and then advancing the fixation device 110 over the implant 120, such as disclosed in commonly owned U.S. Pat. Nos. 8,012,174 and 9,005,246, the subject matter of each of which is herein incorporated by reference. The flexible strand 130 may be captured by implant 120, such as by threading the flexible strand 130 through the eyelet 129 of implant 120. To install the implant 120 with the captured flexible strand 130, implant 120 may be coupled to an operative distal end of a driver or inserter 91 and then placed within the prepared bone hole 99a, 99b until the implant 120 reaches the desired depth. The driver or inserter 91 may be the same as or different from the inserter discussed above with respect to the piggyback fixation piece 200. A rod 92 of the inserter 91 may be received in the cannulation 118 of fixation device 110, and fixation device 110 may then be advanced down rod 92 to be inserted over the implant 120, such as by holding and turning a handle (not shown) of the driver 91. The rod 92 of the driver 91 may have an outer profile, for example, a hex profile, that matches an inner profile of cannulation 118 of fixation device 110, so that rotation of rod 92 also results in rotation of fixation device 110. The inner engagement member 112 of the fixation device also engages the outer engagement member 122 of implant 120, such as via a threaded engagement, as it advances over the implant 120.

Advancement of the fixation device 110 and the relative movement of (e.g., rotation between) the fixation device 110 and the implant 120 is stopped by stopping mechanism 140, such as by the outer threads 122 of the implant 120 reaching the end 113 of the inner threads 112 of fixation device 110. The flexible strand 130 may be threaded through or around the damaged tissue. Thereafter, the fixation device 110 and the implant 120 may be rotated together as a unit to wind the flexible strand 130 captured by the implant 120, thereby reducing any slack (FIG. 6) in the flexible strand 130.

When rotating the fixation device 110 and the implant 120 together, the flexible strand 130 may be wrapped around a portion of the implant 120, as seen in FIG. 3, or around the fixation device 110, as seen in FIG. 5B, or both. In this manner, the flexible strand 130 may be tightened after threading the flexible strand 130 through or around the tissue. Furthermore, when utilized, the construction of bone holes 99*a*, 99*b* forms wider distal regions of the respective bone holes that provide added room or space for the wrapping of the flexible strand 130 around the distal region of the suture anchor assembly. This is in contrast to typical bone holes with more constricted distal regions, where further advancement of the anchor assemblies into those bone holes may be resisted or otherwise restricted after full engagement between the implant 120 and the fixation device 110, due to lack of space. Bone hole constructions according to embodiments of the invention can serve to avoid or significantly decrease torsional forces, frictional resistance, and/or other pressures being applied against the flexible strand 130, the implant 120, and/or the distal region of the fixation device 110 by the wall of the bone hole, and prevent potential damage to the assembly that would otherwise be caused by such added forces or pressures, as the assembly is further advanced into the bone hole and the wrapping of the flexible strand 130 around the suture anchor assembly increases a width of the assembly at its distal end.

In an alternative embodiment, the method may include the step of stacking the piggyback fixation piece 200 on the fixation device 110 as an extension of the fixation device 110 after advancing the fixation device 110 over the implant 120 in the bone hole. These additional steps may be desirable, for example, when the fixation device 110 has been advanced into the bone hole to a point where the distal end of the fixation device 110 has already completely engaged the implant 120 to the stop mechanism 140 and the proximal end of the fixation device is already flush with the surface of the bone, but where there is still laxity in the flexible strand 130 (e.g., as seen in FIG. 5A, prior to attachment of piggyback fixation piece 200). Advancing the suture anchor assembly farther into the bone hole will serve to wrap and wind-up the flexible strand 130 around the suture anchor assembly and reduce slack in the flexible strand 130, but will also cause the proximal end of the fixation device 110 to advance deeper and be recessed from the surface of the bone, reducing cortical fixation. In such situations, the piggyback fixation piece 200 can strengthen and reinforce the fixation between the suture anchor assembly and the bone, where the piggyback fixation piece 200 serves to fill in the recess caused by the additional advancement of the fixation device 110 into the bone hole.

The rod 92 of the inserter 91 may be inserted through the cannulation of the piggyback fixation piece 200 such that the end of rod 92 is exposed or extends away from end 206 by a distance D (FIG. 4). The distance D is generally equal to the depth of the implant 120 in the fixation device's cannulation 118, or in other words, the length of the portion of the fixation device 110 that extends proximal to the end 113 of the inner thread 112, as seen in FIG. 5A, so that the exposed end of rod 92 can be fully inserted into the fixation device 110 with the piggyback fixation piece 200 abutting the fixation device 110, while the implant 120 is also completely engaged with the fixation device 110. Limiting extension of the end of rod 92 to the distance D may be accomplished, for example, via a larger diameter or similar abutment on the inserter 91, or another stop feature between the inserter 91 and the piggyback fixation piece 200. In another embodiment, a different inserter tool can be used that is similar to the initial inserter tool used for advancing the fixation device 110 to the implant 120 at the implant site, where an initial or greatest length of the exposed region of the rod 92 is different (typically shorter compared to the initial inserter tool), corresponding to a total sum of the distance D and a length of the piggyback fixation device 200, so that full insertion or mounting of the piggyback fixation piece 200 over the rod 92 results in a distal extension of the rod 92 substantially equaling the distance D. In still other embodiments, an additional stopping feature may not be needed. The tip or exposed end of rod 92 can then be inserted into the cannulation 118 of the fixation device 110. The entire assembly 100 including the piggyback fixation piece 200 can then be rotated together to advance the anchor assembly 100 further into the bone hole for better securement, as seen in FIG. 5B. Here, the rod 92 may have an outer profile, for example, a hex profile, that matches the inner profiles of both the cannulation of the fixation device 110 and the cannulation of the piggyback fixation piece 200, so that rotation of rod 92 also results in the simultaneous rotation and advancement of both fixation device 110 and piggyback fixation piece 200 further into the bone hole, and wrapping of the flexible strand 130 around the assembly. Preferably, after implantation, the proximal end of the entire assembly 100 is substantially flush with the surface of the bone. If any portion of the piggyback fixation piece 200 protrudes out of the bone hole and above the bone level after the combined assembly 100 is advanced into the bone hole to a desired depth and the flexible strand 130 has been tensioned to a desired amount (e.g., where slack in the flexible strand has been removed), any portion of the piggyback fixation piece 200 remaining outside of the bone hole may be removed, such as by burring down, shaving, or drilling, so that the finally implanted assembly 100 after such removal is substantially flush with the surface of the bone.

Figure 8:
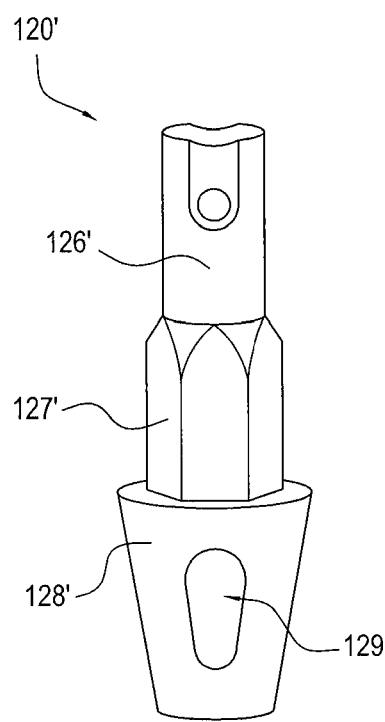
FIG. 8 is a side view of an implant of a slack reducing surgical anchor assembly according to another exemplary embodiment of the present invention.
Figure 9:
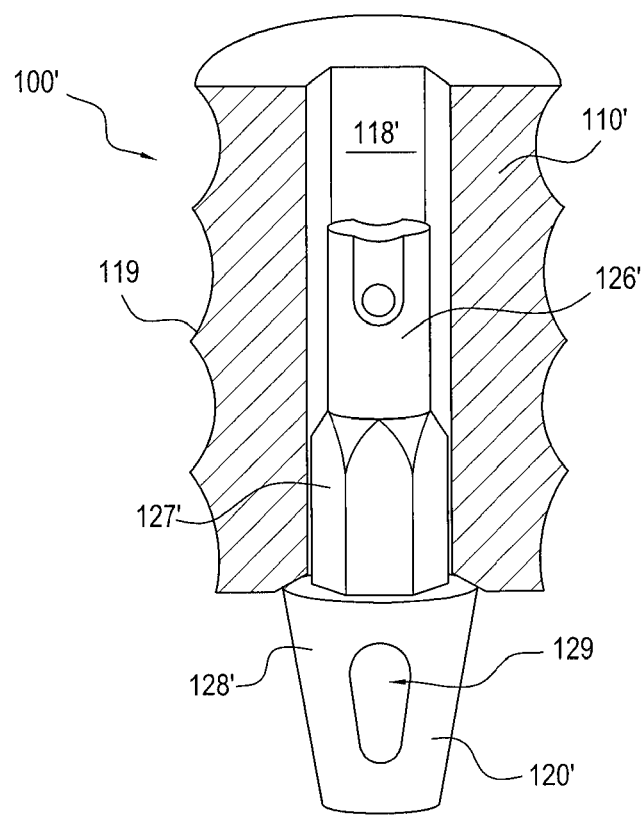
FIG. 9 is an assembled cross-sectional view of the anchor assembly that utilizes the implant of FIG. 8.

FIGS. 8 and 9 illustrate another exemplary embodiment of the present invention.

Parts or portions of the suture anchor assembly described with respect to FIGS. 8 and 9 that are identical or similar to corresponding parts of the previous embodiments will use the same reference numbers, and the descriptions thereof will not be repeated. Suture anchor assembly 100' may generally include a cannulated fixation device 110' with a cannulation 118' extending therethrough and a fixation exterior surface 119 configured to engage bone, such as via a bone hole or bone socket 99*a*, 99*b*, similarly as seen in FIGS. 1A and 1B for the previous embodiments. The cannulation 118' may have an inner profile that matches the inner profile of a rod 92 of an inserter 91, for example, a hex profile, so that when the fixation device 110' is placed around the rod 92, rotation of rod 92 will also result in rotation of the fixation device 110', for advancing fixation device 110' into the bone hole. Fixation exterior surface 119 may comprise, for example, exterior threads or ridges, or be any known anchoring surface, for engaging and anchoring into the bone.

Suture anchor assembly 100' also includes an implant 120' configured to capture one or more repair flexible strands 130, and to be rotatably coupled to the fixation device 110'. Implant 120' may comprise at least a first portion 126', a second portion 127', and a third portion 128'.

First portion 126' may be a shaft that has, for example, a substantially cylindrical cross-section dimensioned to fit in and freely rotate within a tube of rod 92 of inserter or driver 91. The sizing therefore also allows insertion of first portion 126' into cannulation 118' of fixation device 110'. In some embodiments, the first portion 126' may further include a projection or other feature that allows for a releasable snap-in or other temporary fixation of the implant 120' with the rod 92 when the first portion 126' is inserted therein, while still allowing for rotation between the respective parts. In some embodiments, the first portion 126 further includes a transverse through hole or other feature that allows for attachment of a safety suture that is threadable proximally through the driver 91 and attachable, for example, to the handle or other portion at a proximal end of driver 91, to further secure the parts to one another and prevent the implant 120' from inadvertently disconnecting from or falling off of the driver 91.

Second portion 127' is positioned distally to first portion 126', and has an outer engagement feature 122' with a cross-section that is substantially the same as the cross-section of the rod 92, a hex shape in the illustrated embodiment. Therefore, when first portion 126' of implant 120' is inserted in rod 92, rod 92 and implant 120' can be rotatably positioned relative to one another so that their respective hex profiles are aligned. In this manner, as the fixation device 110' is advanced distally over rod 92 and reaches implant 120', fixation device 110' is capable of sliding past the distal end of rod 92 and around the second portion 127' of implant 120' in a form-fit manner, where engagement feature 122' serves as a rotational stop mechanism, so that fixation device 110' and implant 120' are rotatable together in this configuration for wrapping flexible strand 130 around anchor assembly 100' and reducing or eliminating slack in the flexible strand 130. Here, the second portion 127' may be, for example, 7-8 mm in length, so that the second portion 127' has a long enough span to allow for a firm positive engagement between the second portion 127' and the fixation device 110'. In other embodiments, the second portion 127' may be longer or shorter than 7-8 mm, based on the properties and requirements of the particular application. Optimally, the second portion 127' should be short enough to still allow space for sufficient engagement between the rod 92 and fixation device 110', so that the former will still be able to apply a sufficient torqueing force to the latter to further rotate or twist the assembly in the bone hole for at least one half or one (or more) additional turns, as needed, while also being long enough for the fixation device 110' to sufficiently engage and turn the second portion 127' at the same time, for wrapping the flexible strand 130 around the anchor assembly 100' and taking out a desired amount of slack as the entire anchor assembly 100' complex rotates together. In some embodiments, at least one full twist provides a significant amount of additional cable friction with the flexible strand 130 to augment fixation and further secure the anchor assembly 100' in the bone.

Third portion 128' is positioned distally to second portion 127', and may be configured to capture at least one flexible strand 130, via for example, an eyelet 129 or any other structure that is capable of capturing the flexible strand 130.

In some embodiments, a transition between the first portion 126' and the second portion 127' can facilitate sliding of the fixation device 110' over implant 120' and ease engagement or capture of the second portion 127' of implant 120' by the fixation device 110'. This can be accomplished, for example, by a slight circular cross-section that extends distally from the cylindrical first portion 126' and rapidly increases in diameter and transitions in shape, leading into the hex shaped cross-section of the second portion 127'. This or other type of transition can facilitate easier guiding of the inner hex shape of the fixation device 110' over the hex shape of the second portion 127' of implant 120', and prevent, for example, the parts getting stuck or shearing before a full engagement between the parts. In some embodiments another transition between the second portion 127' and the third portion 128' can provide an axial stop that limits insertion of the implant 120' into the cannulation 118' of the fixation device 110'. For example, the third portion 128' can be formed in the shape of a rounded cone, a truncated cone, a trapezoid, or any other appropriate shape, such that the transition to the second portion 127' forms an abutment or ledge by virtue of the proximal end of the third portion 128' having a larger profile than the hex cross-section of the second portion 127'. Such a transition may provide a hard stop against over-insertion of implant 120' into fixation device 110', for example, so that eyelet 129 of third portion 128' remains external to fixation device 110'. Various other types of stops can be employed to limit insertion of the implant 120' into the fixation device 110', for example, a distal region of the second portion 127' having an enlarged hex profile to effect an interference fit with the fixation device 110'.

The embodiment shown in FIGS. 8 and 9 provide an alternative arrangement for rotationally fixing the fixation device 110' with the implant 120', so that rotation of the combined assembly 110' will result in wrapping and reeling in of the flexible strand 130 that is secured to implant 120', to reduce unwanted slack in the flexible strand 130. In a similar manner, other embodiments can also be envisioned, where rotational fixation between a fixation device 110' and implant 120' can facilitate reduction of slack in an anchor assembly.

For example, a similar arrangement can also be applied to a push-type anchor instead of a swivel anchor, so that any existing slack can also be reduced from a flexible strand that is attached to bone via a push anchor using a similar rotating action. Here, all of the features of such an embodiment will be the same or similar to the example in swivel anchor embodiment shown in FIGS. 8 and 9, except that the fixation exterior surface will be arranged to be a plug-type, with for example, ribs or ridges instead of threads, to form a push anchor fixation device. Here, the fixation device still has a hex-shaped cannulation, so that the fixation device can be advanced over and engage the implant in a rotationally fixed manner. Here, the fixation device of the push anchor will be advanced without rotation during implantation, so that a smooth engagement between the parts should be more easily achieved. After the fixation device of the push anchor is engaged with the implant, the combined assembly can be rotated together to wrap the flexible strand or suture around the combined assembly, thereby reducing or eliminating the slack in the flexible strand.

Figure 6:
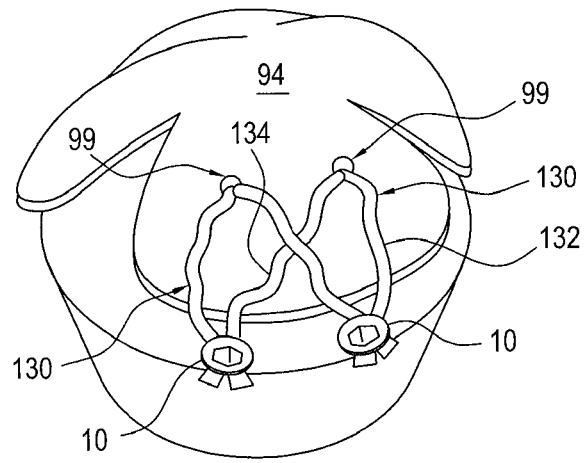
FIG. 6 is a perspective view of a tissue repair construct according to an exemplary embodiment of the present invention, showing the tissue repair construct prior to tightening.

In one exemplary embodiment, the method of tissue repair according to the present invention may be incorporated into known repair techniques, like a bridge repair, such as disclosed in commonly owned U.S. Pat. No. 8,834,521, the subject matter of which is herein incorporated by reference. One or more suture anchor assemblies 100 may be anchored in respective bone holes 99, in the manner described above, in a first medial row. Once the suture anchor assemblies 100 are installed, the tails 132 and 134 of the flexible strands 130 of each assembly 100 may be threaded through the damaged tissue 94 (FIG. 6). The tails 132 and 134 may then be secured in bone holes in a second medial row or lateral row via anchors 10. After all of the anchors have been implanted, any slack or laxity in the flexible strands 130, for example, at the tails 132, 134 that extend between the first medial row of anchors and the second medial row or lateral row of anchors, such as illustrated in FIG. 6, may be eliminated or reduced using a method according to embodiments of the present invention.

Figure 7:
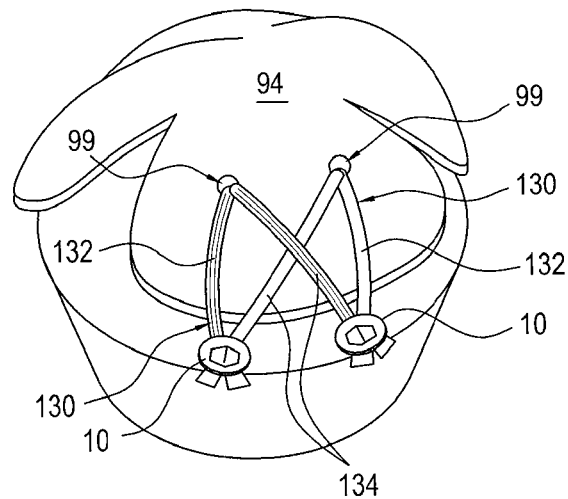
FIG. 7 is a perspective view similar to FIG. 6 showing the tissue repair construct after tightening.

Here, the rod 92 of driver 91 may be reinserted into the proximal end of fixation device 110 and rotated, clockwise for example, to further rotate the combined units 10 including the fixation device 110 and implant 120, typically at the second medial row or lateral row. This reels in or wraps the flexible strands 130 around the suture anchor assembly and winds up and removes the slack in the flexible strands 130 to tighten the bridge repair, as illustrated in FIG. 7. In other embodiments, it may be possible to tighten the suture anchor assemblies in the first medial row in lieu of, or in addition to, tightening of the anchor assemblies in the second medial row or lateral row.

While particular embodiments have been chosen to illustrate the invention, it will be understood by those skilled in the art that various changes and modifications can be made therein without departing from the scope of the invention as defined in the appended claims.

What is claimed is:

1. A surgical anchor assembly, comprising:
   a fixation device having a proximal end, a distal end opposite the proximal end, a cannulation extending through the entire fixation device, a first engagement mechanism at or near the distal end, the first engagement mechanism being formed in a first portion of the cannulation, and a second engagement mechanism formed in a second portion of the cannulation at or near the proximal end, the second engagement mechanism being different than the first engagement mechanism and being configured to engage a driver for installing the fixation device into a bone hole; and
   an implant comprising a first portion connectable to the distal end of the fixation device and having a third engagement mechanism engageable with the first engagement mechanism, and a second portion configured to capture a flexible strand;
   wherein a stop mechanism having at least a portion spaced apart from an end face at the distal end of the fixation device is configured to prevent rotational movement between the fixation device and the implant in at least one direction when the implant is connected to the fixation device.

2. The surgical anchor assembly of claim 1, wherein the first portion of the implant is insertable into the distal end of the fixation device.

3. The surgical anchor assembly of claim 2, wherein the third engagement mechanism is formed on an outer surface of the first portion of the implant.

4. The surgical anchor assembly of claim 1, wherein the first and third engagement mechanisms facilitate a limited rotational connection between the fixation device and the implant, and wherein the stop mechanism is configured to stop the rotational movement facilitated by the first and third engagement mechanisms.

5. The surgical anchor assembly of claim 1, wherein the first and third engagement mechanisms each comprises a thread.

6. The surgical anchor assembly of claim 5, wherein an end of the thread of the first engagement mechanism defines the stop mechanism.

7. The surgical anchor assembly of claim 1, wherein when the implant and the fixation device are connected with the stop mechanism preventing rotation therebetween, the second portion of the implant remains outside of and extends away from the distal end of the fixation device.

8. The surgical anchor assembly of claim 1, wherein the second portion of the implant comprises an eyelet for capturing the flexible strand.

9. The surgical anchor assembly of claim 1, wherein an exterior surface of the fixation device comprises an engagement mechanism for engaging the bone hole.

10. The surgical anchor assembly of claim 9, wherein the engagement mechanism on the exterior surface of the fixation device comprises a thread.

11. A surgical anchor assembly, comprising:
    a fixation device having a proximal end, a distal end, a longitudinal axis extending between the proximal and distal ends, a cannulation extending therethrough, and an exterior surface with a first engagement feature for engaging a bone hole;
    an implant configured to be inserted into the bone hole prior to insertion of the fixation device, the implant comprising a first portion connectable to the distal end of the fixation device in a rotationally fixed manner and a second portion defining a recess that extends transverse to the longitudinal axis for capturing a flexible strand; and
    a separate piggyback fixation piece connectable to the proximal end of the fixation device to extend a total length of the surgical anchor assembly, wherein an exterior surface of the piggyback fixation piece comprises a second engagement feature that is complementary to and substantially the same as the first engagement feature on the exterior surface of the fixation device for engaging the bone hole.

12. The surgical anchor assembly of claim 11, wherein the fixation device and the piggyback fixation piece comprise the same material.

13. The surgical anchor assembly of claim 11, wherein the fixation device and the piggyback fixation piece comprise different materials.

14. The surgical anchor assembly of claim 11, wherein the piggyback fixation piece has a shorter length than a length of the fixation device.

15. The surgical anchor assembly of claim 11, wherein the first and second engagement features each comprises a thread, and wherein the thread of the second engagement feature is alignable with the thread of the first engagement feature.

16. The surgical anchor assembly of claim 11, wherein the implant is rotatably connectable to the fixation device in a limited manner, and wherein a stop mechanism is configured to stop the rotational movement in at least one direction resulting in the rotationally fixed connection.

17. The surgical anchor assembly of claim 8, wherein the entirety of the eyelet of the second portion of the implant remains outside of the distal end of the fixation device.

18. The surgical anchor assembly of claim 11, wherein the piggyback fixation piece has a cannulation therethrough that aligns with the cannulation of the fixation device for receiving a driver.

19. A surgical anchor assembly, comprising:
    a fixation device having a proximal end, a distal end opposite the proximal end, a cannulation extending through the entire fixation device, a first engagement mechanism at or near the distal end, the first engagement mechanism being formed in a first portion of the cannulation, and a second engagement mechanism formed in a second portion of the cannulation at or near the proximal end, the second engagement mechanism being different than the first engagement mechanism and being configured to engage a driver for installing the fixation device into a bone hole; and
    an implant comprising a first portion connectable to the distal end of the fixation device and having a third engagement mechanism engageable with the first engagement mechanism, and a second portion configured to capture a flexible strand;

wherein a stop mechanism is configured to prevent rotational movement between the fixation device and the implant in at least one direction when the implant is connected to the fixation device, and wherein the first engagement mechanism and the third engagement mechanism each comprises a thread and wherein an end of the thread of the first engagement mechanism defines the stop mechanism, thereby limiting rotational movement of the implant relative to the fixation device.

20. The surgical anchor assembly of claim 11, wherein the second portion of the implant comprises an eyelet for capturing the flexible strand.

21. The surgical anchor assembly of claim 19, further comprising a separate piggyback fixation piece connectable to the proximal end of the fixation wherein an exterior surface of the piggyback fixation piece comprises an engagement mechanism that is complementary to an engagement mechanism on the exterior surface of the fixation device.

* * * * *